(12) United States Patent
Sato et al.

(10) Patent No.: US 8,536,469 B2
(45) Date of Patent: Sep. 17, 2013

(54) BODY COMPOSITION MONITOR DETERMINING A DEGREE OF CHANGE RELATIVE TO A PAST BODY COMPOSITION VALUE WHEREIN THE FAVORABLE STAGE ON THE DISPLAY IS OBTAINED EVEN WITH A SLIGHT CHANGE AT THE START OF DIETING, SO THAT A MOTIVATION LEVEL OF THE USER IS INCREASED

(75) Inventors: Tetsuya Sato, Kyoto (JP); Yumi Kitamura, Kyoto (JP); Shinya Tanaka, Kyoto (JP)

(73) Assignee: Omron Healthcare Co., Ltd, Kyoto-shi (JP)

( * ) Notice: Subject to any disclaimer, the term of this patent is extended or adjusted under 35 U.S.C. 154(b) by 543 days.

(21) Appl. No.: 12/866,752

(22) PCT Filed: Mar. 16, 2009

(86) PCT No.: PCT/JP2009/055009
§ 371 (c)(1),
(2), (4) Date: Aug. 9, 2010

(87) PCT Pub. No.: WO2009/116482
PCT Pub. Date: Sep. 24, 2009

(65) Prior Publication Data
US 2010/0312074 A1      Dec. 9, 2010

(30) Foreign Application Priority Data

Mar. 18, 2008   (JP) ................. 2008-069288

(51) Int. Cl.
*A61B 5/053*   (2006.01)
*A61B 5/05*    (2006.01)
*G01G 19/50*   (2006.01)

(52) U.S. Cl.
USPC .............. 177/25.13; 177/25.19; 177/177; 177/245; 600/547

(58) Field of Classification Search
USPC .............. 177/25.13, 25.16, 25.19, 177, 245; 600/547
See application file for complete search history.

(56) References Cited

U.S. PATENT DOCUMENTS 3,967,690 A * 7/1976 Northcutt ................... 177/25.19
4,113,039 A * 9/1978 Ozaki et al. ................ 177/25.19

(Continued)

FOREIGN PATENT DOCUMENTS

CN     1669523 A      9/2005
DE  102 05 823 A1    8/2003

(Continued)

OTHER PUBLICATIONS

Office Action issued in Russian Patent Application No. 2010142318/14(060820) dated Sep. 23, 2011 (with translation).

(Continued)

*Primary Examiner* — Randy W Gibson
(74) *Attorney, Agent, or Firm* — Oliff & Berridge, PLC

(57) ABSTRACT

A body composition monitor of the present invention includes means for inputting a reference value of a body composition component, means for inputting a measurement value of the body composition component, body composition comparison means for comparing the reference value and the measurement value so as to determine a body composition component change amount of the measurement value relative to the reference value, display means provided with a plurality of stages for displaying one of the stages corresponding to the body composition component change amount, and stage determination means provided with a plurality of determination widths respectively corresponding to the plurality of stages for determining one of the stages corresponding to the body composition component change amount with using the plurality of determination widths, wherein the plurality of determination widths are not identical to each other.

8 Claims, 8 Drawing Sheets

(56) References Cited

U.S. PATENT DOCUMENTS

| | | | |
|---|---|---|---|
| 4,366,873 A * | 1/1983 | Levy et al. | 177/25.19 |
| 4,650,014 A * | 3/1987 | Oldendorf et al. | 177/177 |
| 5,817,031 A * | 10/1998 | Masuo et al. | 600/547 |
| 6,354,996 B1 * | 3/2002 | Drinan et al. | 600/300 |
| 6,516,221 B1 * | 2/2003 | Hirouchi et al. | 600/547 |
| 7,979,116 B2 * | 7/2011 | Tseng et al. | 600/547 |
| 8,391,969 B2 * | 3/2013 | Sato | 600/547 |
| 2001/0050683 A1 | 12/2001 | Ishikawa et al. | |
| 2004/0082877 A1 * | 4/2004 | Kouou et al. | 600/546 |
| 2005/0177060 A1 | 8/2005 | Yamazaki et al. | |
| 2005/0187486 A1 * | 8/2005 | Shimomura et al. | 600/547 |
| 2005/0209528 A1 * | 9/2005 | Sato et al. | 600/547 |
| 2006/0206271 A1 | 9/2006 | Oshima et al. | |
| 2009/0204018 A1 * | 8/2009 | Tseng et al. | 600/547 |

FOREIGN PATENT DOCUMENTS

| | | |
|---|---|---|
| DE | 600 11 367 T2 | 6/2005 |
| DE | 600 27 492 T2 | 4/2007 |
| EP | 1 283 024 A1 | 2/2003 |
| EP | 1 095 613 B1 | 6/2004 |
| EP | 1 576 923 A1 | 9/2005 |
| EP | 1 997 426 A1 | 12/2008 |
| JP | A-11-332845 | 12/1999 |
| JP | A-2001-190514 | 7/2001 |
| JP | A-2001-204703 | 7/2001 |
| JP | A-2002-177223 | 6/2002 |
| JP | A-2004-41811 | 2/2004 |
| JP | A-2004-329225 | 11/2004 |
| JP | A-2005-77124 | 3/2005 |
| JP | A-2005-261488 | 9/2005 |
| JP | A-2007-244728 | 9/2007 |
| WO | WO 99/52425 | 10/1999 |
| WO | WO 99/524525 A2 | 10/1999 |
| WO | WO 2007/077650 A1 | 7/2007 |
| WO | WO 2007/108229 A1 | 9/2007 |

OTHER PUBLICATIONS

International Search Report for International Application No. PCT/JP2009/055009, mailed on Jun. 16, 2009 (w/ English translation).

Office Action issued in Chinese Patent Application 200980108404.X dated Aug. 24, 2011 (with translation).

Jun. 2, 2009 International Search Report issued in International Application No. PCT/JP2009/055010 (w/ English Translation).

Sep. 20, 2011 Office Action issued in Russian Application No. 2010142316/00(060818) (w/ English Translation).

Feb. 27, 2013 Office Action issued in U.S. Appl. No. 12/866,808.

Feb. 25, 2013 Office Action issued in German Patent Application No. 11 2009 000 445.8 (with English Translation).

Aug. 12, 2013 Office Action issued in German Patent Application No. 11 2009 000 519.5 (with English translation).

* cited by examiner (A)

(B)

(A)

(B)

(A)

(B)

(A)

(B)

BODY COMPOSITION MONITOR DETERMINING A DEGREE OF CHANGE RELATIVE TO A PAST BODY COMPOSITION VALUE WHEREIN THE FAVORABLE STAGE ON THE DISPLAY IS OBTAINED EVEN WITH A SLIGHT CHANGE AT THE START OF DIETING, SO THAT A MOTIVATION LEVEL OF THE USER IS INCREASED

TECHNICAL FIELD

The present invention relates to a body composition monitor for calculating a body composition value from a measurement value of bioelectrical impedance, and particularly relates to a body composition monitor having a determination function of determining a degree of a change relative to a past body composition value.

BACKGROUND ART

Conventional body composition monitors are described in Patent Documents 1 to 3, for example.

This Patent Document 1 describes that a change in a body weight or a body composition component is displayed in a graph.

Patent Document 2 describes that a change in a body composition component is displayed in a graph.

Patent Document 3 describes that biological information such as body fat is displayed in a graph in chronological order.

Patent Document 1: Japanese Unexamined Patent Publication No. 2001-190514
Patent Document 2: Japanese Unexamined Patent Publication No. 2007-244728
Patent Document 3: Japanese Unexamined Patent Publication No. 2001-204703

DISCLOSURE OF THE INVENTION

Problems to be Solved by the Invention

However, display widths in the graph are equal to each other in such conventional body composition monitors. Thus, when an initial change from a reference time point (such as a measurement start time point) is small, there is a problem that the change is not obviously shown in the graph and a user is less motivated to do body weight reduction or the like.

This invention is achieved focusing on the above problem of the conventional art, and an object thereof is to provide a body composition monitor capable of changing display widths in accordance with stages at the time of displaying a body composition component change amount based on the stages.

Means for Solving the Problems

In order to achieve the above object, the following configurations are adopted in the present invention.

That is, a body composition monitor includes means for inputting a reference value of a body composition component, means for inputting a measurement value of the body composition component, body composition comparison means for comparing the reference value and the measurement value so as to determine a body composition component change amount of the measurement value relative to the reference value, display means provided with a plurality of stages for displaying one of the stages corresponding to the body composition component change amount, and stage determination means provided with a plurality of determination widths respectively corresponding to the plurality of stages for determining one of the stages corresponding to the body composition component change amount with using the plurality of determination widths, wherein the plurality of determination widths are not identical to each other.

The phrase "not identical to each other" indicates not only a case where all the determination widths are differentiated from each other, but also a case where the determination width of at least one stage is differentiated from the determination widths of the other stages. In other words, the plurality of determination widths include determination widths differentiated from each other.

According to this invention, since the determination widths are differentiated, display widths of the display means can be set to have appropriate size as necessary.

When the determination width of the stage corresponding to the body composition component change amount smaller than a predetermined amount is narrower than the determination widths of the other stages, the stage to be displayed can be changed even with the small change amount.

For example, when the determination width of the stage close to the reference value is set to be smaller than the other stages, the user can realize an initial change in body weight reduction or an initial change in body weight increase sooner, and thereby an effect of improving and maintaining motivation of the user to do the body weight reduction can be obtained.

When the determination widths are differentiated in accordance with magnitude of the body composition component change amount, the display widths can be relatively changed in accordance with the magnitude of the body composition component change amount. For example, display stages with small change amounts can be changed to be smaller, or on the other hand, display stages with large change amounts can be set to be hardly changed.

When the determination widths are differentiated in accordance with positive/negative of a difference between the reference value and the measurement value, the display widths can be varied according to the nature of the change. For example, a small display width can be set for a good change and a large display width can be set for a bad change. Thereby, the motivation can be more improved and maintained.

The body composition monitor further includes means for storing the measurement value, wherein a plurality of stored past measurement values may serve as the reference value, and the stages to be displayed may be displayed in a graph in chronological order.

With the body composition monitor including means for inputting a reference value of a body weight, means for inputting a measurement value of the body weight, and body weight comparison means for comparing the reference value and the measurement value so as to determine a body weight change amount of the measurement value relative to the reference value, when the stage determination means determines the stage based on the body composition component change amount and the body weight change amount, a degree of the change in the body composition component is determined not only by the change in the body composition value calculated based on bioelectrical impedance but determined also based on the change in the body weight. Thus, evaluation which more matches with somesthesia of the user can be performed.

Examples of the body composition component include a body fat amount, a body fat percentage, a subcutaneous fat amount, a subcutaneous fat percentage, a visceral fat amount, a visceral fat area, a visceral fat level, a skeletal muscle amount, and a skeletal muscle percentage.

When the body composition component is calculated from a plurality of components selected from the group consisting of the body fat amount, the body fat percentage, the subcutaneous fat amount, the subcutaneous fat percentage, the visceral fat amount, the visceral fat area, the visceral fat level, the skeletal muscle amount, and the skeletal muscle percentage, the evaluation which more matches with the somesthesia of the user can be obtained.

Effect of the Invention

According to the present invention, an effect that the display widths can be changed in accordance with the stages at the time of displaying the body composition component change amount based on the stages can be obtained.

BEST MODE FOR CARRYING OUT THE INVENTION

A preferred embodiment of this invention will be described in detail as an example with reference to the drawings.
(Configuration of Body Composition Monitor)

Figure 1:
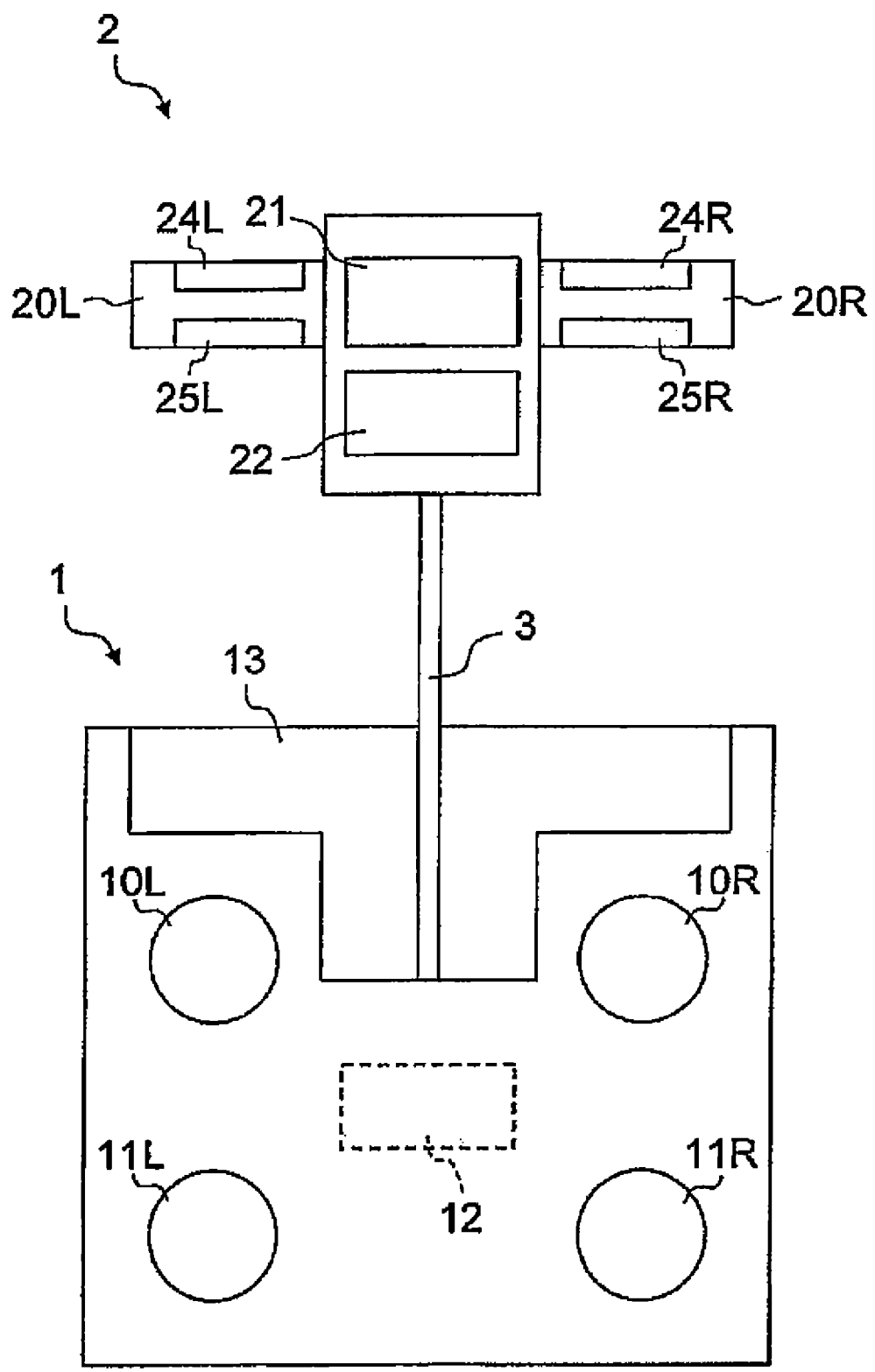
FIG. 1 is a view showing an outer appearance of a body composition monitor according to a first embodiment.

FIG. 1 shows a schematic configuration of the entire body composition monitor. A body weight and body composition monitor which is integrated with a scale will be shown as an example.

This body composition monitor is mainly formed by a main body 1, and a holder (display operation unit) 2. The main body 1 and the holder 2 are connected to each other by a cable 3 so that signals can be sent and received. It should be noted that the main body 1 and the holder 2 may be connected by wireless communication. When not used, the holder 2 and the cable 3 are accommodated in a holder accommodating unit 13 of the main body 1.

Four foot electrodes 10L, 10R, 11L, 11R are provided on an upper surface of the main body 1. The electrodes 10L, 10R are electrodes for applying an electric current to left and right foot soles, and the electrodes 11L, 11R are electrodes for detecting voltage from the left and right foot soles. A body weight measurement unit 12 is built into the main body 1.

Left and right grips 20L, 20R, a display unit 21, an operation unit 22 and the like are provided in the holder 2. The display unit 21 displays a measurement result and guidance and also displays an exercise plan described later, and is for example formed by a LCD display. The operation unit 22 is provided with a user interface for selecting a registration number (user), generating and confirming the exercise plan, and inputting other information. The display unit 21 and the operation unit 22 are preferably formed by shared hardware with using a touchscreen type display.

The grips 20L, 20R are respectively provided with electrodes 24L, 24R for applying the electric current to palms and electrodes 25L, 25R for detecting the voltage from the palms.

Figure 2:
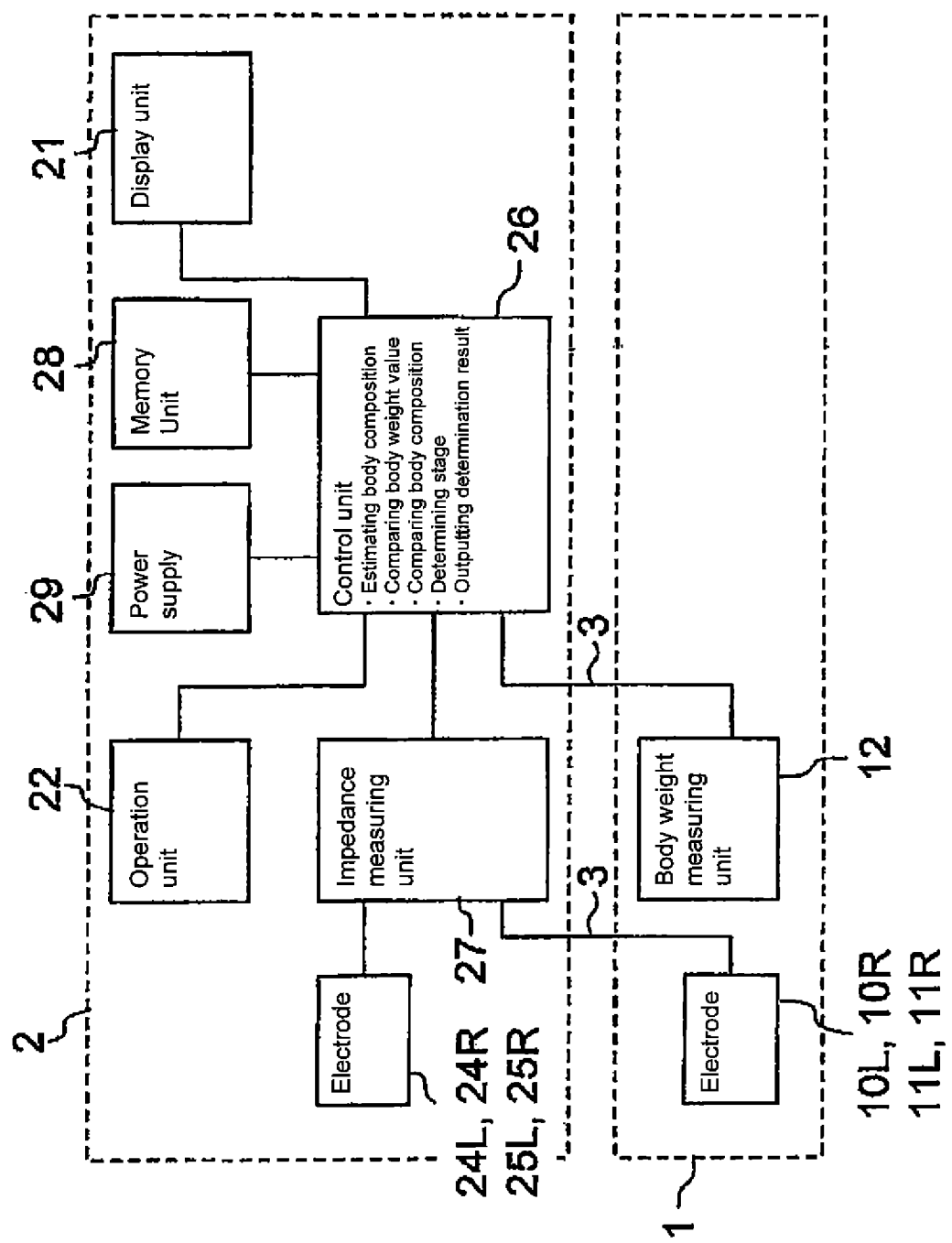
FIG. 2 is a block diagram showing a configuration of the body composition monitor in FIG. 1.

FIG. 2 is a block diagram showing a control configuration of the body composition monitor. As shown in FIG. 2, a control unit 26, an impedance measurement unit 27 serving as means for measuring a body composition, a memory unit 28, a power supply 29 and the like are built into the holder 2.

The display unit 21 is provided with a plurality of stages to be displayed for displaying one of the stages corresponding to a body composition component change amount.

The control unit 26 has a function of inputting a measurement value of a body composition component into the memory unit 28 together with a measuring date and time, a body composition comparison function of comparing the measurement value of the body composition component and a stored reference value so as to determine the body composition component change amount of the measurement value relative to the reference value, a function of inputting a body weight value into the memory unit 28 together with a measuring date and time, a body weight comparison function of comparing the inputted measurement value of the body weight and a stored reference value of the body weight so as to determine a body weight change amount of the measurement value relative to the reference value, a stage determination function of determining the stage to be displayed based on the body composition component change amount and the body weight change amount with using a plurality of determination widths respectively corresponding to the plurality of stages, and a function of outputting a determination result to the display unit 21.

The control unit 26 is formed by a CPU (central processing unit), a memory and the like, and the above functions are realized when the CPU executes a program. However, part or all of the functions of the control unit 26 may be formed by exclusive chips.

The impedance measurement unit 27 is means for applying a predetermined electric current from the foot electrodes 10L, 10R and the hand electrodes 24L, 24R to a living body in accordance with control of the control unit 26, and detecting the voltage by the foot electrodes 11L, 11R and the hand electrodes 25L, 25R so as to measure the impedance inside the body. Specific functions and processing of the control unit 26 and the impedance measurement unit 27 will be described later.

The memory unit 28 is formed by a storage medium such as a nonvolatile memory. The measurement results of the body weight and the body composition (measurement values) and the like are stored in the memory unit 28 for the user (for the registration number) in chronological order by the control unit 26. Specific physical information (gender, age, height) of the user is also stored in the memory unit 28. In the body composition monitor of the present embodiment, a plurality of users (such as four users) can be registered, and any of the users can be selected by designating the registration number by the operation unit 22.

(Body Composition Measurement Function)

Figure 3:
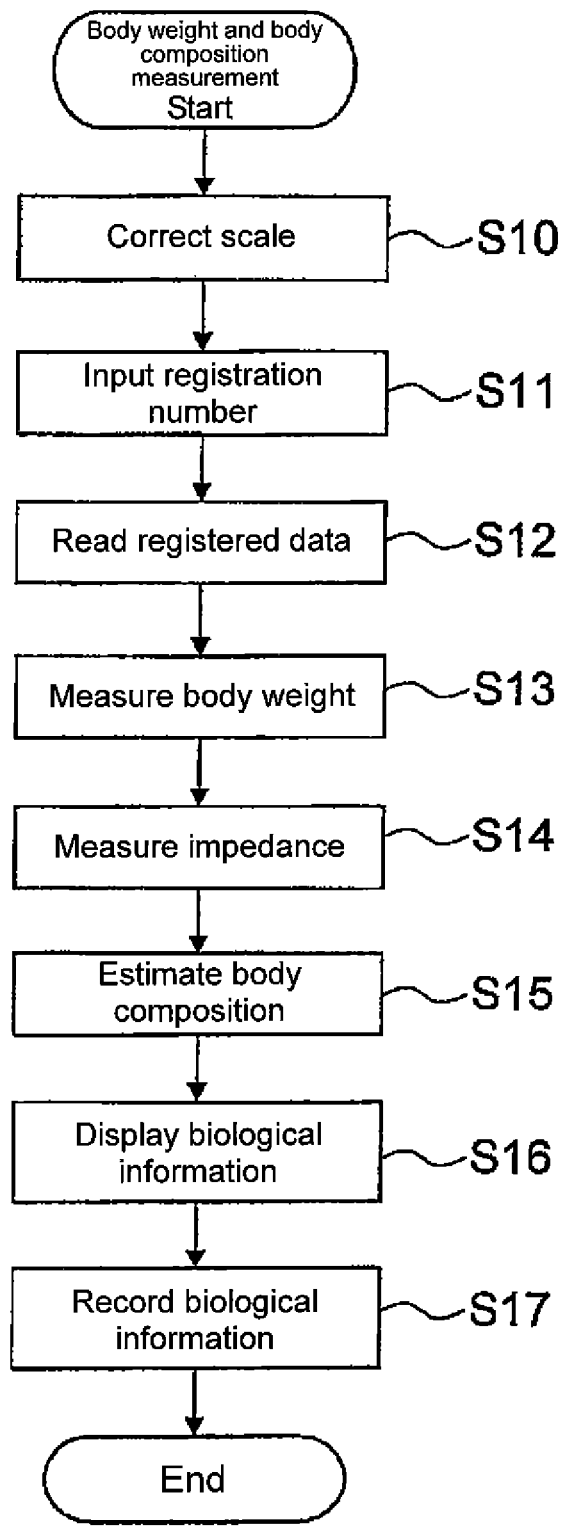
FIG. 3 is a flowchart showing a flow of measurement processing of a body weight and body composition.

With the flowchart of FIG. 3, the flow of standard processing at the time of measuring the body weight and the body composition will be described.

When the user turns ON the body composition monitor, the control unit 26 executes correction processing of a scale (Step S10). After finishing the correction, the user (registration number) can be selected. When the registration number is designated by the user (Step S11), the control unit 26 reads data related to the registration number from the memory unit 28 (Step S12).

When the user steps onto a predetermined position on the main body 1 and stands still in a measuring posture, the body weight measurement unit 12 measures the body weight (Step S13). The impedance measurement unit 27 measures impedance inside the body (Step S14). Measurement values thereof are inputted into the control unit 26.

The control unit 26 estimates the body composition based on the measurement values of the body weight and the impedance and the specific physical information of the user read from the memory unit 28 (Step S15). As the body composition component, for example, a body fat percentage, a body fat amount, a visceral fat percentage, a visceral fat amount, a subcutaneous fat percentage, and a subcutaneous fat amount can be calculated as a fat percentage and a fat amount, and a skeletal muscle percentage, a skeletal muscle amount and the like can be calculated as a muscle percentage and a muscle amount. The body composition can be calculated not only for the entire body but also for each body part such as arms, a trunk, and legs. Further, indicator information which is effective for health management and dieting such as basal metabolism, an obesity rate and body age may be generated based on the calculation results. Since the estimation of the body composition and the calculation of the indicator information can be performed by using the known methods, specific description thereof will not be provided.

The control unit 26 displays biological information such as the body weight, the body composition and the indicator information on the display unit 21 (Step S16). By looking at this display, the user can confirm the measurement results. The control unit 26 stores the biological information in the memory unit 28 together with information on measuring date and time (time stamp) (Step S17). Thereby, values of the biological information are recorded in chronological order.

The data of the body weight and the body composition value of the user stored in the memory unit 28 of one-day old, 7-days old, 30-days old, 90-days old or on a MY reference date can be read out by operating a memory key (not shown) provided in the operation unit 22 for example. The MY reference date indicates a reference date which is set by the user himself/herself.

In the present invention, the control unit 26 compares the measurement value of the body composition component and the stored reference value so as to determine the body composition component change amount of the measurement value relative to the reference value, and also compares the inputted measurement value of the body weight and the stored reference value of the body weight so as to determine the body weight change amount of the measurement value relative to the reference value. With using the plurality of determination widths corresponding to the plurality of display stages, the stage to be displayed is determined based on the body composition component change amount and the body weight change amount, and the determination result is displayed on the display unit 21. The determination widths of the plurality of stages are not identical to each other.

In this embodiment, the determination widths are defined to be two-dimensional areas formed by combining a coordinate axis of the body composition component change amount divided by a plurality of threshold values based on the stages and a coordinate axis of the body weight change amount divided by a plurality of threshold values based on the stages. The threshold value of the area of the determination width is determined to be two-dimensional coordinates with the threshold value of the body composition component change amount and the threshold value of the body weight change amount. For example, even when the coordinates of the divided body composition component change amount are the same but the coordinates of the body weight change amount are different, there are two different areas of the determination widths.

The measurement value of the body composition component and the stored past reference value are compared by determining a difference between the latest measurement value and the reference value serving as the past measurement data so as to determine the body composition component change amount. The measurement value of the body weight and the past reference value are compared by determining a difference between the measurement value and the past reference value so as to determine the body weight change amount. With using the plurality of determination widths corresponding to the plurality of display stages, the stage to be displayed is determined based on the body composition component change amount and the body weight change amount.

The stages basically include three types: status quo; good change; and bad change. The determination widths for the good change are preferably set to be smaller.

The determination width of the stage corresponding to the body composition component change amount smaller than a predetermined amount is preferably set to be narrower than the determination widths of the other stages according to magnitude of the body composition component change amount.

The measurement values of the body composition are changed in accordance with measurement values of the impedance which are varied due to dryness of the hands and the way of gripping. Thus, even when the result is determined to be favorable only with the change amount of the body composition value, the favorable result may be produced due to a measurement error of the impedance, and the result may not correspond to somesthesia. Meanwhile, the body weight is an absolute factor irrespective of the dryness of skin and the way of gripping, and thus the stage of the change amount of the body composition value is determined by combining with the body weight change amount. For example, when the change amount of the skeletal muscle percentage is large but the body weight change amount is large on the positive side, it is thought that the measurement value of the change amount of the skeletal muscle percentage is increased due to the measurement error. Thus, the stage to be displayed is determined to be low and displayed on the display unit 21.

A plurality of determination criteria are set for the body composition values of age, gender, height, body weight and the like, and a relevant determination criterion is selected based on personal information of the user. The determination criteria are stored in the memory unit 28 as evaluation tables.

Figure 4:
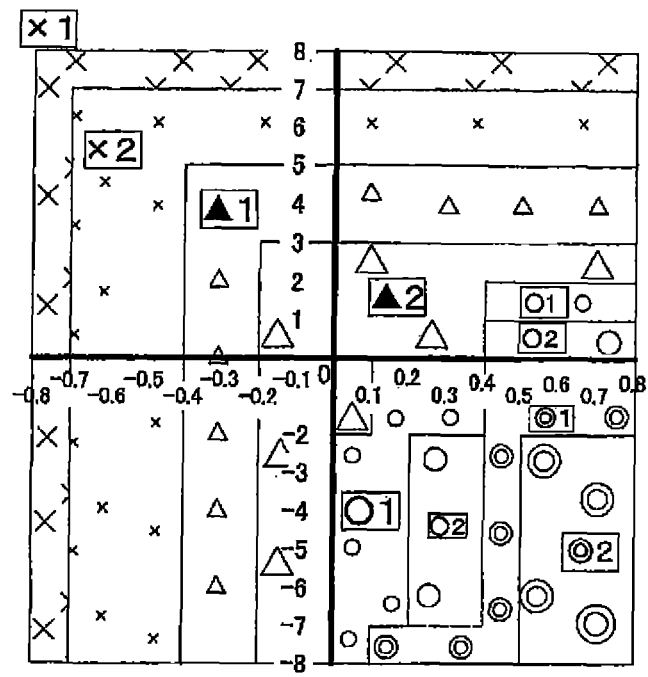
FIG. 4(A) is a view showing a configuration example of a determination table of eight stages for determining a change amount of a skeletal muscle percentage.
FIG. 4(B) is a view showing a configuration example of a determination table of eight stages for determining a change amount of a visceral fat level.
Figure 4:
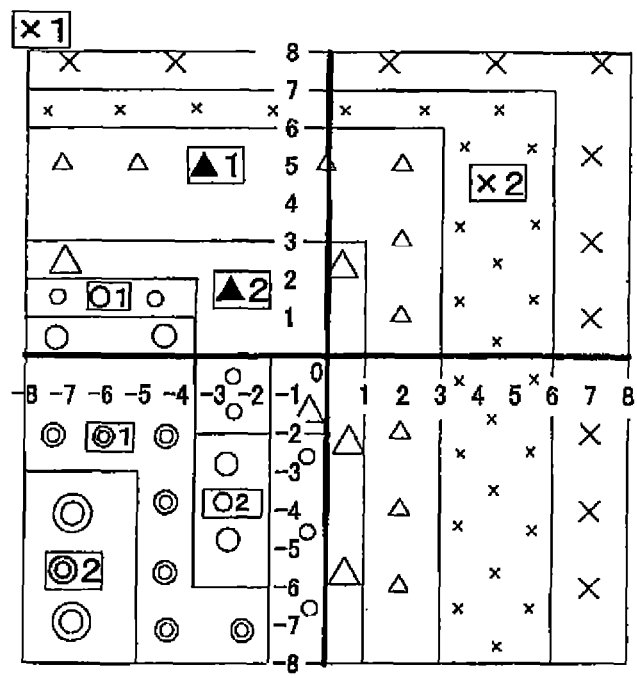

Table 1 is an example of a determination table of eight stages for the skeletal muscle percentage, and FIG. 4(A) is a graph of the determination table showing the change amount of the skeletal muscle percentage on the horizontal axis and a change percentage of the body weight on the vertical axis. The stage to be displayed is determined based on the change amounts of the skeletal muscle percentage and the body weight.

The stages of the skeletal muscle percentage to be displayed basically include four stages of Favorable 2 (◎), Favorable 1 (○), status quo (▲) and Unfavorable (×). In the illustrated example, the stages are respectively divided into first and second levels, so that the stages are divided into eight stages in total.

The skeletal muscle percentage indicates a ratio of skeletal muscles in the body weight. In general, when fat is reduced in dieting, the skeletal muscle percentage is increased.

The change amount of the skeletal muscle percentage (ΔM) from reference time such as dieting start time is determined by "ΔM=M(measurement value of skeletal muscle percentage)−reference value(skeletal muscle percentage at reference time)".

A case where the change amount is decreased (negative) is indicated as Unfavorable, and a case where the change amount is increased (positive) is indicated as Favorable.

The measurement values of the skeletal muscle percentage are changed in accordance with the measurement values of the impedance which are varied due to the dryness of the hands and the way of gripping. Thus, even with the increased skeletal muscle percentage, the favorable result may be produced due to the measurement error, and the result may not correspond to the somesthesia. Meanwhile, the body weight is the absolute factor irrespective of environmental factors such as the dryness of the skin, and thus the stage to be displayed is determined by combining with the body weight change amount.

The change amount of the body weight (ΔW) from the reference time such as the dieting start time is determined by "ΔW=W(measurement value of a body weight)−reference value (body weight at reference time)".

Body weight increase is generally not preferable. Thus, a case where the change percentage is increased (positive) is indicated as Unfavorable, and a case where the change percentage is decreased (negative) is indicated as Favorable.

The skeletal muscle percentage is determined based on the change amount of the skeletal muscle percentage and the body weight change amount.

This is to combine the change amount of the skeletal muscle percentage and the body weight change amount. With a body weight change of zero, two threshold values of 0.1% and 0.4% are available on the positive side, and the stages are divided into three stages of status quo (level 2 (▲2)), Favorable 1 (level 1 (○1)) and Favorable 2 (level 1 (◎1)). The determination width of the status quo stage (level 2 (▲2)) ranges from not less than 0 to less than 0.1%, the determination width of the Favorable 1 stage (level 1 (○1)) ranges from not less than 0.1% to less than 0.4%, and the determination width of the Favorable 2 stage (level 1 (◎1)) is not less than 0.4%. The determination width of the stage closer to the reference value at the start of dieting is set to be smaller than the determination widths of the other stages.

Further, a Favorable 1 stage of level 2 (○2) and a Favorable 2 stage of level 2 (◎2) are also set while adding the body weight.

Meanwhile, three threshold values of −0.2%, −0.4% and −0.7% are available on the negative side, and the stages are divided into four stages of status quo (level 2 (▲2)), status quo (level 1 (▲1)), Unfavorable (level 2 (×2)) and Unfavorable (level 1 (×1)).

The determination width of the status quo stage (level 2 (▲2)) ranges from not less than −0.2% to less than 0, the determination width of the status quo stage (level 1 (▲1)) ranges from not less than −0.4% to less than −0.2%, the determination width of the Unfavorable stage (level 2 (×2)) ranges from not less than −0.7 to less than −0.4%, and the determination width of the Unfavorable stage (level 1 (×1)) is less than −0.7%. The determination widths of the status quo stages (level 2 (▲2) and level 1 (▲1)) closer to the reference value at the start of dieting are set to be smaller than the determination width of the Unfavorable stage (level 2 (×2)).

With regard to the status quo stage (level 2 (▲2)) in the vicinity of the reference value (0), the determination widths are differentiated in accordance with positive/negative of the difference between the reference value and the measurement value. The determination width of the status quo stage (level 2 (▲2)) on the positive side which indicates the good change is as small as 0.1%, and the determination width of the status quo stage (level 2 (▲2)) on the negative side which indicates the bad change is as large as 0.2%.

Figure 6:
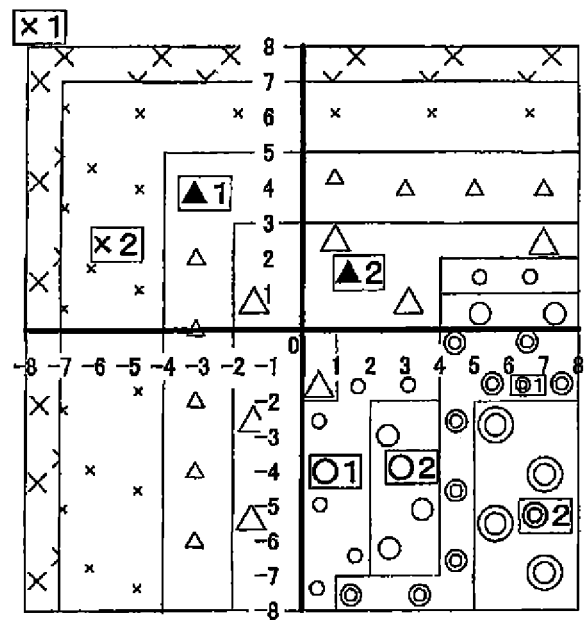
FIG. 6(A) is a view showing a configuration example of a determination table of eight stages for determining a change amount a ratio between of the skeletal muscle percentage and a subcutaneous fat percentage.
FIG. 6(B) is a view showing a configuration example of a determination table of twelve stages for determining the change amount of the ratio between the skeletal muscle percentage and the subcutaneous fat percentage.
Figure 6:
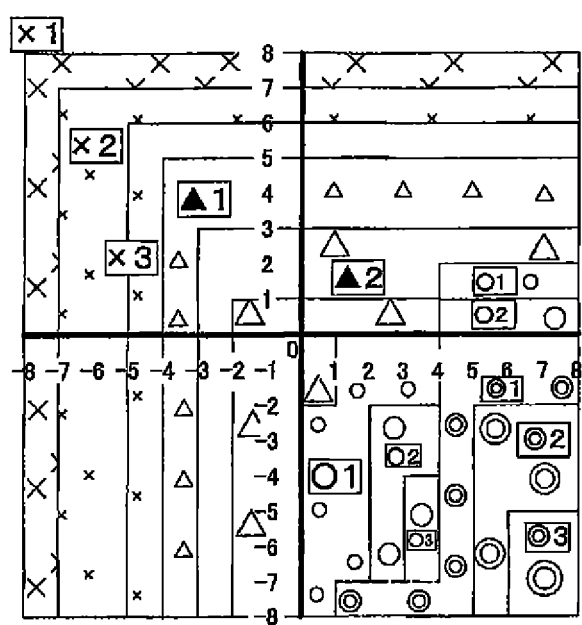

Table 3 is an example of a determination table of a difference between a measurement value and a reference value regarding a ratio between the skeletal muscle percentage and the subcutaneous fat percentage as the body composition component calculated from a plurality of components, and FIG. 6(A) is a graph of the determination table showing a change amount of the ratio between the skeletal muscle percentage and the subcutaneous fat percentage on the horizontal axis and the change percentage of the body weight on the vertical axis. The stage to be displayed is determined based on the skeletal muscle percentage and the change percentage of the body weight.

The stages of the ratio between the skeletal muscle percentage and the subcutaneous fat percentage to be displayed basically include four stages of Favorable 2 (◎), 1 (○), status quo (▲) and Unfavorable (×). In the illustrated example, the stages are respectively divided into first and second levels, so that the stages are divided into eight stages in total.

In general, when the body weight is reduced in dieting, subcutaneous fat is reduced. Thus, the ratio between the skeletal muscle percentage and the subcutaneous fat percentage is increased. Therefore, a case where the change percentage is decreased (negative) is indicated as Unfavorable, and a case where the change amount is increased (positive) is indicated as Favorable.

The measurement values of this ratio are also changed in accordance with the measurement values of the impedance which are varied due to the dryness of the hands and the way of gripping. Thus, even when the result is determined to be Favorable 2 (◎) or 1 (○), the favorable result may be produced due to the measurement error of the impedance, and evaluation on the change in the skeletal muscle percentage is corrected by combining with evaluation on the change in the body weight.

The ratio between the skeletal muscle percentage and the subcutaneous fat percentage is determined based on the change amount of the ratio between the skeletal muscle percentage and the subcutaneous fat percentage and the body weight change amount.

This is to combine the change amount of the ratio between the skeletal muscle percentage and the subcutaneous fat percentage and the body weight change amount. With the body weight change of zero, two threshold values of 1% and 4% are available on the positive side, and the stages are divided into three stages of status quo of level 2 (▲2), Favorable 1 of level 1 (○1) and Favorable 2 of level 1 (⊙1). The determination width of the status quo stage of level 2 (▲2) ranges from not less than 0 to less than 1%, the determination width of the Favorable 1 stage of level 1 (○1) ranges from not less than 1% to less than 4%, and the determination width of the Favorable 2 stage of level 1 (⊙1) is not less than 4%. The determination width of the stage closer to the reference value at the start of dieting is set to be smaller than the determination widths of the other stages.

Further, a Favorable 1 stage of level 2 (○2) and a Favorable 2 stage of level 2 (⊙2) are also set while adding the body weight.

Meanwhile, three threshold values of −2%, −4% and −7% are available on the negative side, and the stages are divided into four stages of status quo of level 2 (▲2), status quo of level 1 (▲1), Unfavorable of level 2 (×2) and Unfavorable of level 1 (×1).

The determination width of the status quo stage of level 2 (▲2) ranges from not less than −2% to less than 0, the determination width of the status quo stage of level 1 (▲1) ranges from not less than −4% to less than −2%, the determination width of the Unfavorable stage of level 2 (×2) ranges from not less than −7 to less than −4%, and the determination width of the Unfavorable stage of level 1 (×1) is less than −7%. The determination widths of the status quo stages of level 2 (▲2) and level 1 (▲1) closer to the reference value at the start of dieting are set to be smaller than the determination width of the Unfavorable stage of level 2 (×2).

With regard to the status quo stage of level 2 (▲2) in the vicinity of the reference value (0), the determination widths are differentiated in accordance with positive/negative of the difference between the reference value and the measurement value. The determination width of the status quo stage of level 2 (▲2) on the positive side which indicates the good change is as small as 1%, and the determination width of the status quo stage of level 2 (×2) on the negative side which indicates the bad change is as large as 2%.

Table 2 is an example of a determination table of eight stages for the visceral fat level, and FIG. 4(B) is a graph of the determination table showing a change amount of the visceral fat level on the horizontal axis and the change percentage of the body weight on the vertical axis. The stage to be displayed is determined based on the change amounts of the visceral fat level and the body weight.

The visceral fat level is an indicator for sectional areas of the visceral fat, including one to 30 levels at 0.5 intervals.

The stages of the visceral fat level to be displayed also basically include four stages of Favorable 2 (⊙), 1 (○), status quo (▲) and Unfavorable (×). In the illustrated example, the stages are respectively divided into levels 1, 2, so that the stages are divided into eight stages in total.

In general, when the body weight is reduced in dieting, the visceral fat level is reduced. Thus, a case where the visceral fat level is increased is indicated as Unfavorable, and a case where the visceral fat level is decreased is indicated as Favorable.

The change amount of the visceral fat level ($\Delta$VFA) from the reference time such as the dieting start time is determined by "$\Delta$VFA=VFA (measurement value of visceral fat level)−reference value (visceral fat level at reference time)".

A case where the change amount is decreased (negative) is indicated as Unfavorable, and a case where the change amount is increased (positive) is indicated as Favorable.

The measurement values of the visceral fat level are also changed in accordance with the measurement values of the impedance which are varied due to the dryness of the hands and the way of gripping. Thus, even with the increased skeletal muscle percentage, the favorable result may be produced due to the measurement error, and the result may not correspond to the somesthesia. Meanwhile, the body weight is the absolute factor irrespective of the environmental factors such as the dryness of the skin, and thus the stage to be displayed is determined by combining with the body weight change amount.

The change amount of the body weight ($\Delta$W) from the reference time such as the dieting start time is determined by "$\Delta$W=W (measurement value of a body weight)−reference value (body weight at reference time)".

The body weight increase is generally not preferable. Thus, the case where the change percentage is increased (positive) is indicated as Unfavorable, and the case where the change percentage is decreased (negative) is indicated as Favorable.

The visceral fat level is determined based on the change amounts of the visceral fat level and the body weight.

This is to combine the change amount of the visceral fat level and the body weight change amount. With the body weight change of zero, two threshold values of −1.5 and −3.5 are available on the negative side, and the stages are divided into three stages of status quo of level 2 (▲2), Favorable 1 of level 1 (○1) and Favorable 2 of level 1 (⊙1). The determination width of the status quo stage of level 2 (▲2) ranges from not less than −1.5 to less than 0, the determination width of the Good stage of level 1 (○1) ranges from not less than −3.5 to less than −1.5, and the determination width of the Favorable 2 stage of level 1 (⊙1) is less than −3.5. The determination width of the stage closer to the reference value at the start of dieting is set to be smaller than the determination widths of the other stages.

Further, a Favorable 1 stage of level 2 (○2) and a Favorable 2 stage of level 2 (⊙2) are also set while adding the body weight.

Meanwhile, three threshold values of 1, 3 and 6 are available on the positive side, and the stages are divided into four stages of status quo of level 2 (▲2), status quo of level 1 (▲1), Unfavorable of level 2 (×2) and Unfavorable of level 1 (×1).

The determination width of the status quo stage of level 2 (▲2) ranges from not less than 0 to less than 1, the determination width of the status quo stage of level 1 (▲1) ranges from not less than 1 to less than 3, the determination width of the Unfavorable stage of level 2 (×2) ranges from not less than 3 to less than 6, and the determination width of the Unfavorable stage of level 1 (×1) is not less than 6. The determination widths of the status quo stages of level 2 (▲2) and level 1 (▲1) closer to the reference value at the start of dieting are set to be smaller than the determination width of the Unfavorable stage of level 2 (×2).

With regard to the status quo stage of level 2 (▲2) in the vicinity of the reference value (0), the determination widths are differentiated in accordance with positive/negative of the difference between the reference value and the measurement value. The determination width of the status quo stage of level 2 (▲2) on the negative side which indicates the good change is −1.5, and the determination width of the status quo stage of level 2 (▲2) on the positive side which indicates the bad change is as small as 1. However, when including the determination width of the status quo stage of level 1 (▲1), the determination width is set to be large.

The determination tables of Tables 1 to 3 are varied for example in accordance with gender, age, height and the like, and determination tables are produced for each gender and each age and stored in the memory unit 28. The corresponding evaluation tables are referred in accordance with registered data of the user, so that the change in the body composition is determined.

Table 4 shows a comprehensive determination result produced by combining the change in the skeletal muscle percentage and the change in the visceral fat level, a MY DIET determination result. A comprehensive health level can be determined by comprehensively determining the visceral fat level and the skeletal muscle percentage.

Such comprehensive determination is not limited to this example but may be performed with body composition components calculated from a plurality of components selected from the group consisting of the body fat amount, the body fat percentage, the subcutaneous fat amount, the subcutaneous fat percentage, the visceral fat amount, the visceral fat area, the visceral fat level, the skeletal muscle amount, and the skeletal muscle percentage.

The control unit 26 outputs evaluation results of the changes of the body composition determined as above, and displays the results on the display unit 21.

Figure 7:
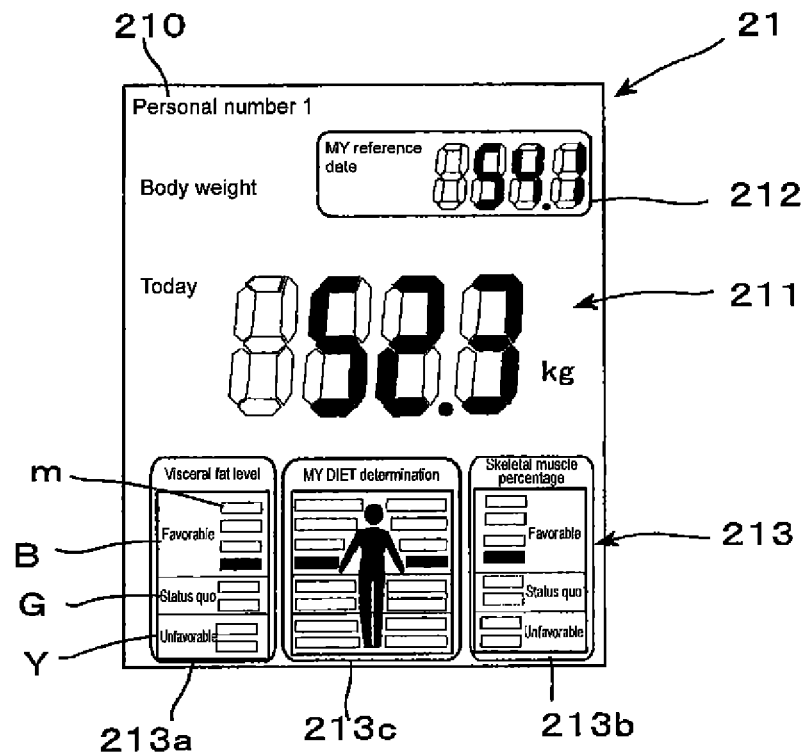
FIG. 7(A) is a view showing a screen configuration example of a display unit of eight stages.
FIG. 7(B) is a view showing a screen configuration example of the display unit of twelve stages.
Figure 7:
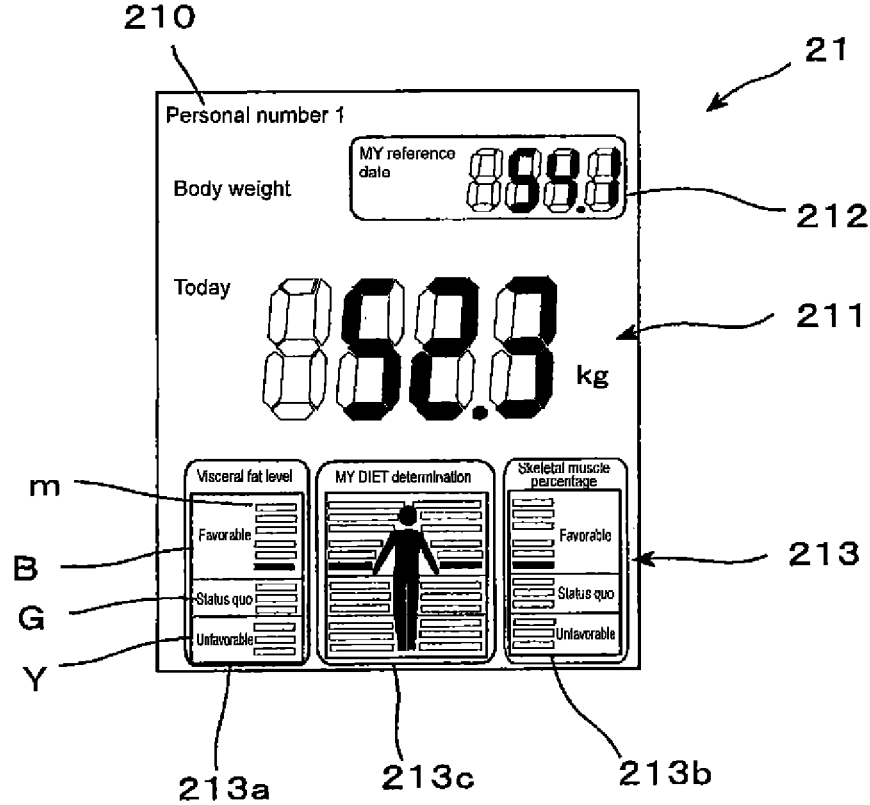

Firstly, with reference to FIG. 7(A), a screen configuration of the display unit 21 will be briefly described.

A personal number 210, a measurement data display field 211 of current measurement data, a measurement data display field 212 of past measurement data stored in the memory unit 28, and a determination display field 213 of the body composition are provided in the display unit 21.

In the illustrated example, three fields including a visceral fat level determination display field 213a, a skeletal muscle percentage determination display field 213b, a MY DIET determination display field 213c regarding the ratio between the skeletal muscle percentage and the subcutaneous fat percentage are provided in the determination display field 213. The comprehensive determination result of the skeletal muscle percentage and the visceral fat level which is shown in Table 4 may be displayed on this MY DIET determination display field 213c.

The determination display fields 213a, 213b, 213c respectively have a Favorable area B, a status quo area G, and an Unfavorable area Y. Four display marks m can be displayed on the Favorable area B, two display marks can be displayed on the status quo area G, and two display marks can be displayed on the Unfavorable area Y. The Favorable area B is divided into a Favorable 2 area B1 and a Favorable area B2.

A human icon is displayed on the MY DIET determination display field 213c, and a body part such as arms, legs, and a trunk can be displayed.

Next, the display of this display unit 21 will be briefly described.

With regard to the measurement data of the user, current body weight is firstly displayed on the measurement data display field 211. When a display switch key (not shown) is pressed, the kind of the body composition displayed on the measurement data display field 211 of the current measurement data is switched. Meanwhile, when a memory key (not shown) is pressed, the past measurement data of the body composition is read out from the memory unit 28 and displayed on the measurement data display field 212 of the past measurement data. The display is switched to show the past measurement data of one-day old, 7-days old, 30-days old, 90-days old and on the MY reference date, respectively. The MY reference date indicates a reference date which is set by the user himself/herself. The display may be automatically switched without the memory key.

A difference between the current measurement data and the past measurement data is calculated and a difference between the measurement data of the body weight is calculated. Then, the corresponding determination table stored in the memory is read out, the change amounts of the body composition and the body weight are compared with the threshold values of the determination table so as to select the corresponding determination result, and a determination signal is generated and outputted based on the determination result. Based on the outputted determination signal, the display mark m is displayed on the corresponding evaluation area (the Favorable area B, the status quo area G or the Unfavorable area Y) of the determination display field of the display unit 21. At this time, the light may be emitted on the background color.

In the illustrated example, not only the determination result is displayed on the skeletal muscle percentage determination display field 213b but also the change amounts of the measurement data regarding the visceral fat level and the MY DIET determination are calculated at the same time and the determination results are displayed on the visceral fat level determination display field 213a and the MY DIET determination display field 213c. However, the results are not necessarily displayed all together. Only the determination result of the displayed body composition, that is, the skeletal muscle percentage in this example, may be displayed.

Although not shown, the stepwise display of the data of one-day old, 7-days old, 30-days old, 90-days old and on the MY reference date may be changed to graph display in chronological order.

Figure 5:
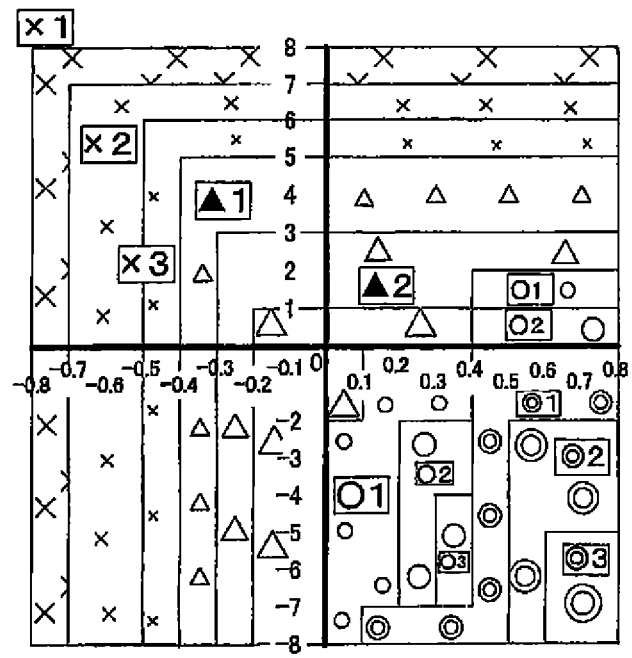
FIG. 5(A) is a view showing a configuration example of a determination table of twelve stages for determining the change amount of the skeletal muscle percentage.
FIG. 5(B) is a view showing a configuration example of a determination table of twelve stages for determining the change amount of the visceral fat level.
Figure 5:
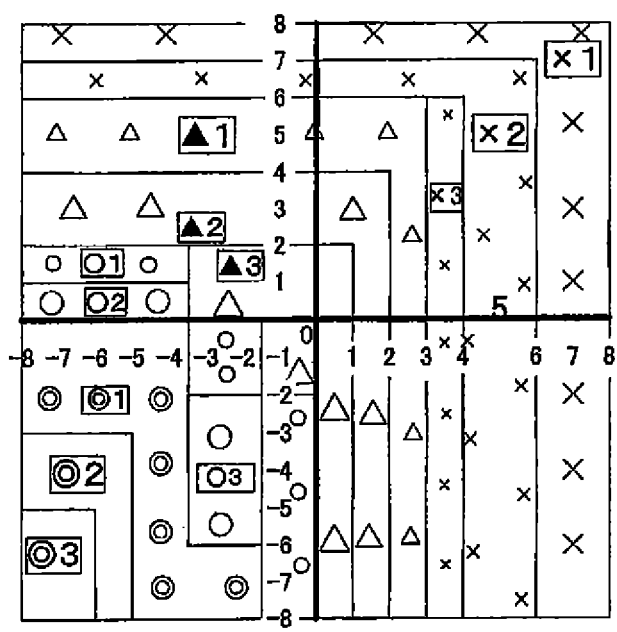

Tables 5 to 7 are examples of determination tables for displaying the change amount of the skeletal muscle percentage, the change amount of the ratio between the skeletal muscle percentage and the subcutaneous fat, and the change amount of the visceral fat level on twelve stages, and FIGS. 5(A), 5(B) and 6(B) are graphs showing contents of these determination tables.

As well as the eight-stage display, this twelve-stage display includes four stages of Favorable 2 (☉), Favorable 1 (○), status quo (▲) and Unfavorable (×), and the stages are respectively divided into first, second and third levels, so that the stages are divided into twelve stages in total. Determination is basically the same as the above determination of the eight stages, and only different points will be described.

Firstly, with regard to the skeletal muscle percentage, as shown in Table 5 and FIG. 5(A), with the body weight change of zero, two threshold values of 0.1% and 0.4% are available on the positive side, and the stages are divided into three stages of status quo of level 2 (▲2), Favorable 1 of level 1 (○1) and Favorable 2 of level 1 (☉1).

In this example, as the different points, the Favorable 1 stage of level 2 (○2) is further divided so as to set a Favorable 1 stage of level 3 (○3), and the Favorable 2 stage of level 2 (☉2) is further divided so as to set an Favorable 2 stage of level 3 (☉3).

Meanwhile, threshold values of −0.3% and −0.5% are additionally provided on the negative side. The status quo stages of level 1 and level 2 of the eight-stage display are divided into two so as to set status quo stages of level 1 to level 3 (▲1, ▲2, ▲3), and further the Unfavorable stage of level 2 (×2) of the eight-stage display is divided into two so as to set the Unfavorable stages of level 1 to level 3 (×1, ×2, ×3).

Next, with regard to the ratio between the skeletal muscle percentage and the subcutaneous fat percentage, as shown in Table 6 and FIG. 6(B), with the body weight change of zero, two threshold values of 1% and 4% are available on the positive side, and the stages are divided into three stages of status quo of level 2 (▲2), Favorable 1 of level 1 (○1) and Favorable 2 of level 1 (☉1).

In this example, as the different points, the Favorable 1 stage of level 2 (○2) is further divided so as to set a Favorable 1 stage of level 3 (○3), and the Favorable 2 stage of level 2 (⊙2) is further divided so as to an Favorable 2 stage of level 3 (⊙3).

Meanwhile, threshold values of −3% and −5% are additionally provided on the negative side. The status quo stages of level 1 and level 2 of the eight-stage display are divided into two so as to set status quo stages of level 1 to level 3 (▲1, ▲2, ▲3), and further the Unfavorable stage of level 2 (×2) of the eight-stage display is divided into two so as to set the Unfavorable stages of level 1 to level 3 (×1, ×2, ×3).

Next, with regard to the visceral fat level, as shown in Table 7 and FIG. 5(B), with the body weight change of zero, two threshold values of −1.5 and −3.5 are available on the negative side, and the stages are divided into three stages of status quo of level 2 (▲2), Favorable 1 of level 1 (○1) and Favorable 2 of level 1 (⊙1).

In this example, as the different points, the Favorable 1 stage of level 2 (○2) of the eight-stage display serves as a Favorable 1 stage of level 3 (○3), and the Favorable 2 stage of level 2 (⊙2) is further divided so as to set an Favorable 2 stage of level 3 (⊙3).

Meanwhile, threshold values of 2 and 4 are additionally provided on the positive side. The status quo stage of level 1 of the eight-stage display is divided so as to set the status quo stages of level 1 to level 3 (▲1, ▲2, ▲3), and further the Unfavorable stage of level 2 (×2) of the eight-stage display is divided into two so as to set the Unfavorable stages of level 1 to level 3 (×1, ×2, ×3).

With regard to the screen configuration of the display unit 21, six display marks m can be displayed on the Favorable area B, three display marks can be displayed on the status quo area G, and three display marks can be displayed on the Unfavorable area Y of the determination display fields 213a, 213b, 213c. The Favorable area B is divided into the Favorable 2 area B1 and the Favorable area B2.

Figure 8:
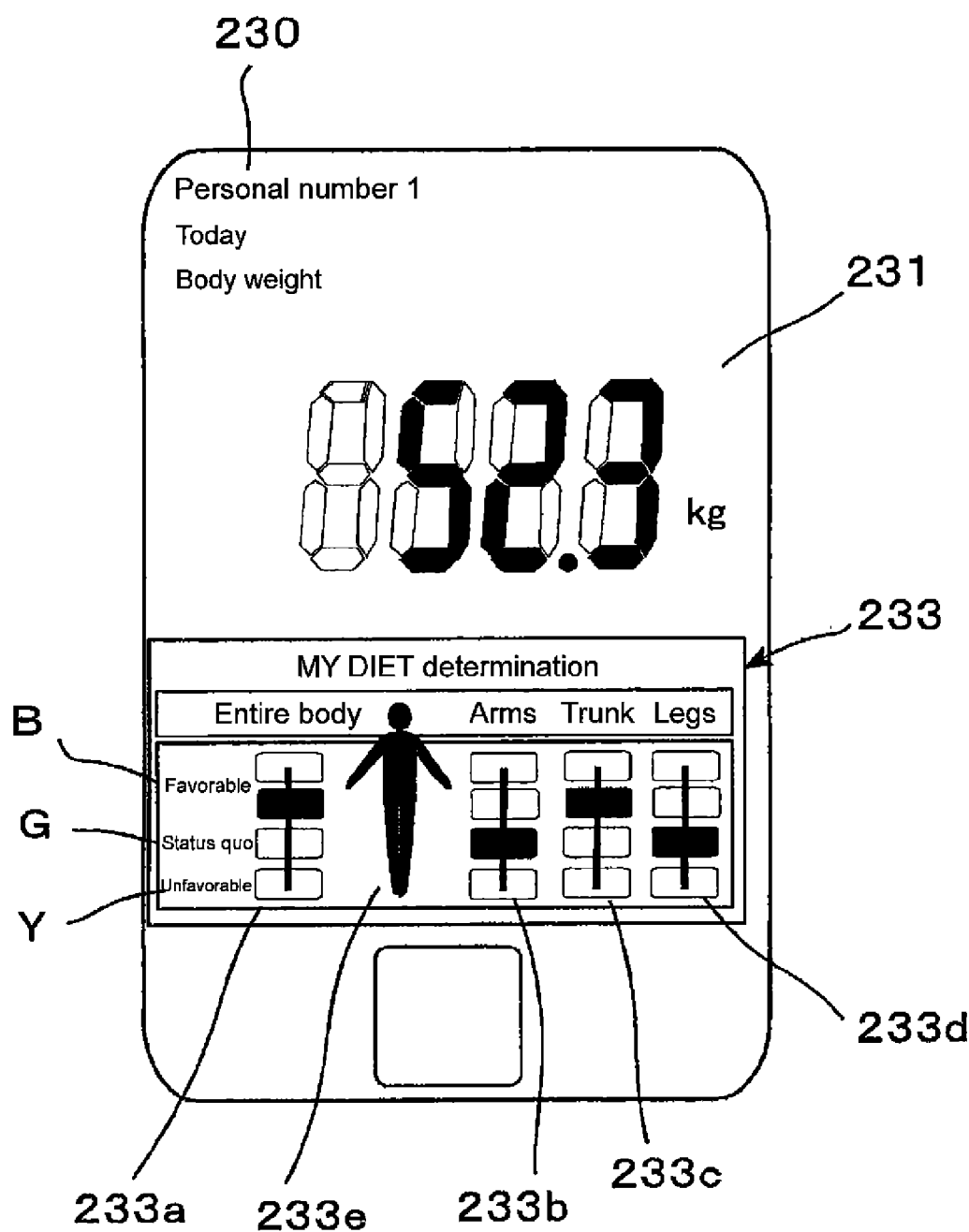
FIG. 8 is a view showing another screen configuration example of the display unit.

FIG. 8 shows another screen configuration example of the display unit 21.

A personal number 230 of the user, a data display field 231 and a determination display field 233 of the body composition are provided in the display unit 21.

In the illustrated example, determination display fields 233a, 233b, 233c, 233d are respectively provided for four body parts including the entire body, the arms, the trunk, and the legs, and a human icon 233e is displayed. As a matter of course, change amounts of other body composition may be determined. In the illustrated example, only the MY DIET determination regarding the ratio between the skeletal muscle percentage and the subcutaneous fat percentage is available as the body composition to be determined.

The rectangular display marks m are displayed on the Favorable area B, the status quo area G and the Unfavorable area Y on the determination display fields 233a, 233b, 233c, 233d. The light may be emitted or blinked for each of the body parts including the arms, the legs, and the trunk of the human icon 233e so as to distinguish evaluation contents.

In this example, the ratio between the skeletal muscle percentage and the subcutaneous fat percentage for each of the body parts including the entire body, the arms, the trunk, and the legs is calculated from the measured impedance as the body composition and stored in the memory 28 as the measurement data together with the measuring date and time.

The data on the measurement data display unit 231 is switched to the data of one-day old, 7-days old, 30-days old, 90-days old and on the MY reference date, respectively, by switching the memory key or the like (not shown). In the illustrated example, the body weight may be displayed or other body composition may be displayed on the data display field 231.

The change amount between the current data and the past data of the ratio between the skeletal muscle percentage and the subcutaneous fat percentage for each of the body parts and the body weight change amount are calculated in accordance with this reference date, and the determination table read out from the memory unit 28 is referred so as to determine the stage to be displayed.

In the illustrated example, four stages including two Favorable stages, one status quo stage and one Unfavorable stage are displayed. As a matter of course, as well as the above examples, the display stages may be divided into eight or twelve. Although not particularly shown in the drawings, with regard to the determination of the display stages, the determination tables as described above are set, and the determination width of the stage closer to the reference value such as the determination width of the status quo stage is set to be smaller than the determination width of the Favorable stage.

The display signal is outputted in accordance with this determination result, and the display mark is displayed on the corresponding evaluation area for each of the body parts on the MY DIET determination display field. The light may be blinked or emitted for the corresponding part of the human icon at the same time.

Since the determination width of the status quo stage is set to be smaller than other determination widths, not the status quo stage but the Favorable 1 stage of level 2 can be displayed even with a slight change at the start of dieting, so that motivation of the user is maintained or increased.

It should be noted that the above embodiment only shows one specific example of the present invention. The scope of the present invention is not limited to the above embodiment but may be variously modified within the technological scope thereof.

For example, in the above embodiment, the skeletal muscle percentage, the ratio between the skeletal muscle percentage and the subcutaneous fat percentage, and the visceral fat level are described as examples of the body composition component. However, various body composition information such as the body fat amount, the body fat percentage, the subcutaneous fat amount, the subcutaneous fat percentage, the visceral fat amount, the visceral fat area, the visceral fat level, the skeletal muscle amount, and the skeletal muscle percentage can be selected. The processing flows and the display screens in the above embodiment are only one specific example and may be appropriately modified as long as similar results and effects can be obtained.

TABLE 1

| Determination | Skeletal muscle percentage difference (Δ% MUSCLE) | | Body weight difference (Δ WEIGHT) |
| --- | --- | --- | --- |
| Unfavorable (X 1) | Δ% MUSCLE < −0.7 | OR | 7 ≦ Δ WEIGHT |
| Unfavorable (X 2) | −0.7 ≦ Δ% MUSCLE < −0.4 | AND | Δ WEIGHT < 7 |
|  | −0.4 ≦ Δ% MUSCLE | AND | 5 ≦ Δ WEIGHT < 7 |

TABLE 1-continued

| Determination | Skeletal muscle percentage difference (Δ% MUSCLE) | | Body weight difference (Δ WEIGHT) |
|---|---|---|---|
| Status quo (▲1) | −0.4 ≤ Δ% MUSCLE < −0.2 | AND | Δ WEIGHT < 5 |
|  | −0.2 ≤ Δ% MUSCLE | AND | 3 ≤ Δ WEIGHT < 5 |
| Status quo (▲2) | −0.2 ≤ Δ% MUSCLE < 0 | AND | Δ WEIGHT < 3 |
|  | 0 ≤ Δ% MUSCLE < 0.1 | AND | −2 ≤ Δ WEIGHT < 3 |
|  | 0.1 ≤ Δ% MUSCLE < 0.4 | AND | 0 ≤ Δ WEIGHT < 3 |
|  | 0.4 ≤ Δ% MUSCLE | AND | 2 ≤ Δ WEIGHT < 3 |
| Favorable 1 (○1) | 0 ≤ Δ% MUSCLE < 0.1 | AND | Δ WEIGHT < −2 |
|  | 0.1 ≤ Δ% MUSCLE < 0.2 | AND | −7 ≤ Δ WEIGHT < 0 |
|  | 0.2 ≤ Δ% MUSCLE < 0.4 | AND | −2 ≤ Δ WEIGHT < 0 |
|  | 0.4 ≤ Δ% MUSCLE | AND | 1 ≤ Δ WEIGHT < 2 |
| Favorable 1 (○2) | 0.2 ≤ Δ% MUSCLE < 0.4 | AND | −7 ≤ Δ WEIGHT < −2 |
|  | 0.4 ≤ Δ% MUSCLE | AND | 0 ≤ Δ WEIGHT < 1 |
| Favorable 2 (⊙1) | 0.1 ≤ Δ% MUSCLE < 0.4 | AND | Δ WEIGHT < −7 |
|  | 0.4 ≤ Δ% MUSCLE < 0.5 | AND | Δ WEIGHT < 0 |
|  | 0.5 ≤ Δ% MUSCLE | AND | −2 ≤ Δ WEIGHT < 0 |
| Favorable 2 (⊙2) | 0.5 ≤ Δ% MUSCLE | AND | Δ WEIGHT < −2 |

TABLE 2

| Determination of visceral fat level | Visceral fat level difference (ΔVFA) | | Body weight difference (Δ WEIGHT) |
|---|---|---|---|
| Unfavorable (X1) | 6 ≤ Δ VFA | OR | 7 ≤ Δ WEIGHT |
| Unfavorable (X2) | 3 ≤ Δ VFA < 6 | AND | Δ WEIGHT < 7 |
|  | Δ VFA < 3 | AND | 6 ≤ Δ WEIGHT < 7 |
| Status quo (▲1) | 1 ≤ Δ VFA < 3 | AND | Δ WEIGHT < 6 |
|  | Δ VFA < 1 | AND | 4 ≤ Δ WEIGHT < 6 |
| Status quo (▲2) | 0 ≤ Δ VFA < 1 | AND | Δ WEIGHT < 3 |
|  | −1.5 ≤ Δ VFA < 0 | AND | −2 ≤ Δ WEIGHT < 3 |
|  | −3.5 ≤ Δ VFA < −1.5 | AND | 0 ≤ Δ WEIGHT < 3 |
|  | Δ VFA ≤ −3.5 | AND | 2 ≤ Δ WEIGHT < 3 |
| Favorable 1 (○1) | −1.5 ≤ Δ VFA < 0 | AND | Δ WEIGHT < −2 |
|  | −3.5 ≤ Δ VFA < −1.5 | AND | −2 ≤ Δ WEIGHT < 0 |
|  | Δ VFA ≤ −3.5 | AND | 1 ≤ Δ WEIGHT < 2 |
| Favorable 1 (○2) | −3.5 ≤ Δ VFA < −1.5 | AND | −6 ≤ Δ WEIGHT < −2 |
|  | Δ VFA ≤ −3.5 | AND | 0 ≤ Δ WEIGHT < 1 |
| Favorable 2 (⊙1) | −3.5 ≤ Δ VFA < −1.5 | AND | Δ WEIGHT < −6 |
|  | −5 ≤ Δ VFA < −3.5 | AND | Δ WEIGHT < 0 |
|  | Δ VFA < −5 | AND | −3 ≤ Δ WEIGHT < 0 |
| Favorable 2 (⊙2) | Δ VFA < −5 | AND | Δ WEIGHT < −3 |

TABLE 3

| Determination | Difference of ratio between skeletal muscle percentage and subcutaneous fat percentage (Δp) | | Body weight difference (Δ WEIGHT) |
|---|---|---|---|
| Unfavorable (X1) | Δp < −7 | OR | 7 ≤ Δ WEIGHT |
| Unfavorable (X2) | −7 ≤ Δp < −4 | AND | Δ WEIGHT < 7 |
|  | −4 ≤ Δp | AND | 5 ≤ Δ WEIGHT < 7 |
| Status quo (▲1) | −4 ≤ Δp < −2 | AND | Δ WEIGHT < 5 |
|  | −2 ≤ Δp | AND | 3 ≤ Δ WEIGHT < 5 |
| Status quo (▲2) | −2 ≤ Δp < 0 | AND | Δ WEIGHT < 3 |
|  | 0 ≤ Δp < 1 | AND | −2 ≤ Δ WEIGHT < 3 |
|  | 1 ≤ Δp < 4 | AND | 0 ≤ Δ WEIGHT < 3 |
|  | 4 ≤ Δp | AND | 2 ≤ Δ WEIGHT < 3 |
| Favorable 1 (○1) | 0 ≤ Δp < 1 | AND | Δ WEIGHT < −2 |
|  | 1 ≤ Δp < 2 | AND | −7 ≤ Δ WEIGHT < 0 |
|  | 2 ≤ Δp < 4 | AND | −2 ≤ Δ WEIGHT < 0 |
|  | 4 ≤ Δp | AND | 1 ≤ Δ WEIGHT < 2 |
| Favorable 1 (○2) | 2 ≤ Δp < 4 | AND | −7 ≤ Δ WEIGHT < −2 |
|  | 4 ≤ Δp | AND | 0 ≤ Δ WEIGHT < 1 |
| Favorable 2 (⊙1) | 1 ≤ Δp < 4 | AND | Δ WEIGHT < −7 |
|  | 4 ≤ Δp < 5 | AND | Δ WEIGHT < 0 |
|  | 5 ≤ Δp | AND | −2 ≤ Δ WEIGHT < 0 |
| Favorable 2 (⊙2) | 5 ≤ Δp | AND | Δ WEIGHT < −2 |

TABLE 4

| Determination of visceral fat level | Determination of skeletal muscle percentage | Comprehensive determination |
|---|---|---|
| Unfavorable (X) | X | X |
| | ▲ | ▲ |
| | ○ | ▲ |
| | ⊙ | |
| Status quo (▲) | X | X |
| | ▲ | ▲ |
| | ○ | ○ |
| | ⊙ | ○ |
| Favorable 1 (○) | X | ▲ |
| | ▲ | ○ |
| | ○ | |
| | ⊙ | |
| Favorable 2 (⊙) | X | ▲ |
| | ▲ | ○ |
| | ○ | ⊙ |
| | ⊙ | |

TABLE 5

| Determination | Skeletal muscle percentage difference (Δ% MUSCLE) | | Body weight difference (Δ WEIGHT) |
|---|---|---|---|
| Unfavorable (X 1) | Δ% MUSCLE < −0.7 | OR | 7 ≦ WEIGHT |
| Unfavorable (X 2) | −0.7 ≦ Δ% MUSCLE < −0.5 | AND | Δ WEIGHT < 7 |
| | −0.5 ≦ Δ% MUSCLE | AND | 6 ≦ Δ WEIGHT < 7 |
| Unfavorable (X 3) | −0.5 ≦ Δ% MUSCLE < −0.4 | AND | 5 ≦ Δ WEIGHT |
| | −0.4 ≦ Δ% MUSCLE | AND | 5 ≦ Δ WEIGHT < 6 |
| Status quo (▲ 1) | −0.4 ≦ Δ% MUSCLE < −0.3 | AND | Δ WEIGHT < 5 |
| | −0.3 ≦ Δ% MUSCLE | AND | 3 ≦ Δ WEIGHT < 5 |
| Status quo (▲ 2) | −0.3 ≦ Δ% MUSCLE < −0.2 | AND | Δ WEIGHT < 3 |
| | −0.2 ≦ Δ% MUSCLE < 0.4 | AND | 1 ≦ Δ WEIGHT < 3 |
| | −0.4 ≦ Δ% MUSCLE | AND | 2 ≦ Δ WEIGHT < 3 |
| Status quo (▲ 3) | −0.2 ≦ Δ% MUSCLE < 0 | AND | Δ WEIGHT < 1 |
| | 0 ≦ Δ% MUSCLE < 0.1 | AND | −2 ≦ Δ WEIGHT < 1 |
| | 0.1 ≦ Δ% MUSCLE < 0.4 | AND | 0 ≦ Δ WEIGHT < 1 |
| Favorable 1 (○ 1) | 0 ≦ Δ% MUSCLE < 0.1 | AND | Δ WEIGHT < −2 |
| | 0.1 ≦ Δ% MUSCLE < 0.2 | AND | −7 ≦ Δ WEIGHT < 0 |
| | 0.2 ≦ Δ% MUSCLE < 0.4 | AND | −2 ≦ Δ WEIGHT < 0 |
| | 0.4 ≦ Δ% MUSCLE | AND | 1 ≦ Δ WEIGHT < 2 |
| Favorable 1 (○ 2) | 0.2 ≦ Δ% MUSCLE < 0.3 | AND | −7 ≦ Δ WEIGHT < −2 |
| | 0.2 ≦ Δ% MUSCLE < 0.4 | AND | −4 ≦ Δ WEIGHT < −2 |
| | 0.4 ≦ Δ% MUSCLE | AND | 0 ≦ Δ WEIGHT < 1 |
| Favorable 1 (○ 3) | 0.3 ≦ Δ% MUSCLE < 0.4 | AND | −7 ≦ Δ WEIGHT < −4 |
| Favorable 2 (⊙ 1) | 0.1 ≦ Δ% MUSCLE < 0.4 | AND | Δ WEIGHT < −7 |
| | 0.4 ≦ Δ% MUSCLE < 0.5 | AND | Δ WEIGHT < 0 |
| | 0.5 ≦ Δ% MUSCLE | AND | −2 ≦ Δ WEIGHT < 0 |
| Favorable 2 (⊙ 2) | 0.5 ≦ Δ% MUSCLE < 0.6 | AND | Δ WEIGHT < −2 |
| | 0.6 ≦ Δ% MUSCLE | AND | −5 ≦ Δ WEIGHT < −2 |
| Favorable 2 (⊙ 3) | 0.6 ≦ Δ% MUSCLE | AND | Δ WEIGHT < −5 |

TABLE 6

| Determination | Difference of ratio between skeletal muscle percentage and subcutaneous fat percentage (Δp) | | Body weight difference (Δ WEIGHT) |
|---|---|---|---|
| Unfavorable (X 1) | Δp < −7 | OR | 7 ≦ Δ WEIGHT |
| Unfavorable (X 2) | −0.7 ≦ Δp < −5 | AND | Δ WEIGHT < 7 |
| | −5 ≦ Δp | AND | 6 ≦ Δ WEIGHT < 7 |
| Unfavorable (X 3) | −5 ≦ Δp < −4 | AND | Δ WEIGHT < 6 |
| | −4 ≦ Δp | AND | 5 ≦ Δ WEIGHT < 6 |
| Status quo (▲ 1) | −4 ≦ Δp < −3 | AND | Δ WEIGHT < 5 |
| | −3 ≦ Δp | AND | 3 ≦ Δ WEIGHT < 5 |
| Status quo (▲ 2) | −3 ≦ Δp < −2 | AND | Δ WEIGHT < 3 |
| | −2 ≦ Δp < 4 | AND | 1 ≦ Δ WEIGHT < 3 |
| | 4 ≦ Δp | AND | 2 ≦ Δ WEIGHT < 3 |
| Status quo (▲ 3) | −2 ≦ Δp < 0 | AND | Δ WEIGHT < 1 |
| | 0 ≦ Δp < 1 | AND | −2 ≦ Δ WEIGHT < 1 |
| | 1 ≦ Δp < 4 | AND | 0 ≦ Δ WEIGHT < 1 |
| Favorable 1 (○ 1) | 0 ≦ Δp < 1 | AND | Δ WEIGHT < −2 |
| | 1 ≦ Δp < 2 | AND | −7 ≦ Δ WEIGHT < 0 |
| | 2 ≦ Δp < 4 | AND | −2 ≦ Δ WEIGHT < 0 |
| | 4 ≦ Δp | AND | 1 ≦ Δ WEIGHT < 2 |
| Favorable 1 (○ 2) | 2 ≦ Δp < 3 | AND | −7 ≦ Δ WEIGHT < −2 |
| | 2 ≦ Δp < 4 | AND | −4 ≦ Δ WEIGHT < −2 |
| | 4 ≦ Δp | AND | 0 ≦ Δ WEIGHT < 1 |

TABLE 6-continued

| Determination | Difference of ratio between skeletal muscle percentage and subcutaneous fat percentage ($\Delta p$) | | Body weight difference ($\Delta$ WEIGHT) |
|---|---|---|---|
| Favorable 1 (○ 3) | $3 \leq \Delta p < 4$ | AND | $-7 \leq \Delta$ WEIGHT $< -4$ |
| Favorable 2 (⊙ 1) | $1 \leq \Delta p < 4$ | AND | $\Delta$ WEIGHT $< -7$ |
| | $4 \leq \Delta p < 5$ | AND | $\Delta$ WEIGHT $< 0$ |
| | $5 \leq \Delta p$ | AND | $-2 \leq \Delta$ WEIGHT $< 0$ |
| Favorable 2 (⊙ 2) | $5 \leq \Delta p < 6$ | AND | $\Delta$ WEIGHT $< -2$ |
| | $6 \leq \Delta p$ | AND | $-5 \leq \Delta$ WEIGHT $< -2$ |
| Favorable 2 (⊙ 3) | $6 \leq \Delta p$ | AND | $\Delta$ WEIGHT $< -5$ |

TABLE 7

| Determination of visceral fat level | Visceral fat level difference ($\Delta$VFA) | | Body weight difference ($\Delta$ WEIGHT) |
|---|---|---|---|
| Unfavorable (X 1) | $6 \leq \Delta$VFA | OR | $7 \leq \Delta$ WEIGHT |
| Unfavorable (X 2) | $4 \leq \Delta$VFA $< 6$ | AND | $\Delta$ WEIGHT $< 7$ |
| | $\Delta$VFA $< 4$ | AND | $6 \leq \Delta$WEIGHT $< 7$ |
| Unfavorable (X 3) | $3 \leq \Delta$VFA $< 4$ | AND | $\Delta$ WEIGHT $< 6$ |
| Status quo (▲ 1) | $2 \leq \Delta$VFA $< 3$ | AND | $\Delta$ WEIGHT $< 6$ |
| | $\Delta$VFA $< 2$ | AND | $4 \leq \Delta$ WEIGHT $< 6$ |
| Status quo (▲ 2) | $1 \leq \Delta$VFA $< 2$ | AND | $\Delta$ WEIGHT $< 4$ |
| | $\Delta$VFA $< 1$ | AND | $2 \leq \Delta$ WEIGHT $< 4$ |
| Status quo (▲ 3) | $0 \leq \Delta$VFA $< 1$ | AND | $\Delta$ WEIGHT $< 2$ |
| | $-1.5 \leq \Delta$VFA $< 0$ | AND | $-2 \leq \Delta$ WEIGHT $< 2$ |
| | $-3.5 \leq \Delta$VFA $< -1.5$ | AND | $0 \leq \Delta$ WEIGHT $< 2$ |
| Favorable 1 (○ 1) | $-1.5 \leq \Delta$VFA $< 0$ | AND | $\Delta$ WEIGHT $< -2$ |
| | $-3.5 \leq \Delta$VFA $< -1.5$ | AND | $-2 \leq \Delta$ WEIGHT $< 0$ |
| | $\Delta$VFA $\leq -3.5$ | AND | $1 \leq \Delta$ WEIGHT $< 2$ |
| Favorable 1 (○ 2) | $\Delta$VFA $\leq -3.5$ | AND | $1 \leq \Delta$ WEIGHT $< 2$ |
| Favorable 1 (○ 3) | $-3.5 \leq \Delta$VFA $< -1.5$ | AND | $-6 \leq \Delta$ WEIGHT $< -2$ |
| Favorable 2 (⊙ 1) | $-3.5 \leq \Delta$VFA $< -1.5$ | AND | $\Delta$ WEIGHT $< -6$ |
| | $-5 \leq \Delta$VFA $< -3.5$ | AND | $\Delta$ WEIGHT $< 0$ |
| | $\Delta$VFA $\leq -5$ | AND | $-2 \leq \Delta$ WEIGHT $< 0$ |
| Favorable 2 (⊙ 2) | $-6 \leq \Delta$VFA $< -5$ | AND | $\Delta$ WEIGHT $< -2$ |
| | $\Delta$VFA $\leq -6$ | AND | $-5 \leq \Delta$ WEIGHT $< -2$ |
| Favorable 2 (⊙ 3) | $\Delta$VFA $\leq -6$ | AND | $\Delta$ WEIGHT $< -5$ |

DESCRIPTION OF SYMBOLS

1 main body
2 holder
3 cable
10L, 10R, 11L, 11R foot electrode
12 body weight measurement unit
13 holder accommodating unit
20L, 20R grip
21 display unit
22 operation unit
24L, 24R, 25L, 25R hand electrode
26 control unit
27 impedance measurement unit
28 memory unit
29 power supply
210 user number
211 display field of current measurement data
212 display field of past measurement data
213 determination display field
213a determination display field (visceral fat level)
213b determination display field (skeletal muscle percentage)
213c determination display field (MY DIET)
233 determination display field of body composition
233a determination display field (entire body)
233b determination display field (arms)
233c determination display field (trunk)
233d determination display field (legs)
B favorable
G status quo
Y unfavorable

The invention claimed is:

1. A body composition monitor, comprising:
means for inputting a reference value of a body composition component;
means for inputting a measurement value of the body composition component;
body composition comparison means for comparing the reference value and the measurement value so as to determine a body composition component change amount of the measurement value relative to the reference value;
display means provided with a plurality of stages for displaying one of the stages corresponding to the body composition component change amount; and
stage determination means provided with a plurality of determination widths respectively corresponding to the plurality of stages for determining one of the stages corresponding to the body composition component change amount with using the plurality of determination widths, wherein
each of the plurality of determination widths is a range defined by the body composition component change amount divided by one of a plurality of threshold values based on the plurality of stages, and
the plurality of determination widths are not identical to each other.

2. The body composition monitor according to claim 1, wherein the determination width of the stage corresponding to the body composition component change amount smaller than a predetermined amount is narrower than the determination widths of the other stages.

3. The body composition monitor according to claim 1, wherein the determination widths are differentiated in accordance with magnitude of the body composition component change amount.

4. The body composition monitor according to claim 1, wherein the determination widths are differentiated in accordance with a positive and a negative change in the body composition component change amount.

5. The body composition monitor according to claim 1, further comprising:
   means for storing the measurement value, wherein
   a plurality of past measurement values each serve as the reference value, and the stages are displayed in a graph in chronological order.

6. The body composition monitor according to claim 1, comprising:
   means for inputting a reference value of a body weight;
   means for inputting a measurement value of the body weight; and
   body weight comparison means for comparing the reference value and the measurement value so as to determine a body weight change amount of the measurement value relative to the reference value, wherein
   the stage determination means determines the stage based on the body composition component change amount and the body weight change amount.

7. The body composition monitor according to claim 1, wherein the body composition component indicates a body fat amount, a body fat percentage, a subcutaneous fat amount, a subcutaneous fat percentage, a visceral fat amount, a visceral fat area, a visceral fat level, a skeletal muscle amount, or a skeletal muscle percentage.

8. The body composition monitor according to claim 1, wherein the body composition component is calculated from a plurality of components selected from the group consisting of the body fat amount, the body fat percentage, the subcutaneous fat amount, the subcutaneous fat percentage, the visceral fat amount, the visceral fat area, the visceral fat level, the skeletal muscle amount, and the skeletal muscle percentage.

* * * * *